(12) United States Patent
Yacoubian

(10) Patent No.: US 8,918,193 B2
(45) Date of Patent: Dec. 23, 2014

(54) HEART WIRE

(76) Inventor: Vahe S. Yacoubian, Glendale, CA (US)

( * ) Notice: Subject to any disclaimer, the term of this patent is extended or adjusted under 35 U.S.C. 154(b) by 1889 days.

(21) Appl. No.: 11/839,337

(22) Filed: Aug. 15, 2007

(65) Prior Publication Data

US 2008/0046061 A1 Feb. 21, 2008

Related U.S. Application Data

(60) Provisional application No. 60/822,563, filed on Aug. 16, 2006.

(51) Int. Cl.
*A61N 1/36* (2006.01)
*A61N 1/05* (2006.01)

(52) U.S. Cl.
CPC ............. *A61N 1/0587* (2013.01); *A61N 1/059* (2013.01); *A61N 1/0595* (2013.01)
USPC ......................................... 607/130; 607/129

(58) Field of Classification Search
CPC .... A61N 1/0587; A61N 1/059; A61N 1/0595
USPC .......................................... 607/119, 129, 130
See application file for complete search history.

(56) References Cited

U.S. PATENT DOCUMENTS

| | | |
|---|---|---|
| 3,902,501 A | 9/1975 | Citron et al. |
| 3,939,843 A | 2/1976 | Smyth |
| 4,166,469 A | 9/1979 | Littleford |
| 4,338,947 A | 7/1982 | Williams |
| 4,809,713 A | 3/1989 | Grayzel |
| 4,883,070 A | 11/1989 | Hanson |
| 4,938,231 A | 7/1990 | Milijasevic et al. |
| 4,962,767 A | 10/1990 | Brownlee |
| 5,090,422 A | 2/1992 | Dahl et al. |
| 5,127,421 A | 7/1992 | Bush et al. |
| 5,255,692 A | 10/1993 | Neubauer et al. |
| 5,261,419 A | 11/1993 | Osypka |
| 5,314,463 A | 5/1994 | Camps et al. |

(Continued)

FOREIGN PATENT DOCUMENTS

| | | |
|---|---|---|
| JP | 03-112566 A | 5/1991 |
| JP | 07-222807 A | 8/1995 |

(Continued)

OTHER PUBLICATIONS

English language translation of JP 2001-087397.*

(Continued)

*Primary Examiner* — Tammie K Heller
(74) *Attorney, Agent, or Firm* — Kenneth L. Green

(57) ABSTRACT

An apparatus including a pledget; and an anchor disposed through the pledget in a manner to form a loop over a surface of the pledget, wherein the anchor comprises electrically conductive material. A kit including a pledget; an anchor of an electrically conductive material including at least one end having a structure capable of puncturing myocardial tissue; and a heart wire. A method including placing an electrically conductive portion of a heart wire between a pledget and an anchor coupling the pledget to a heart of a patient; and establishing conductive contact between the anchor and the heart wire. An advantage of the apparatus and method is that an anchor may be placed in healthy myocardial tissue and a heart wire electrically connected to the anchor may be removed with minimal risk of bleeding.

12 Claims, 12 Drawing Sheets

(56) References Cited

U.S. PATENT DOCUMENTS

| | | | |
|---|---|---|---|
| 5,356,427 | A | 10/1994 | Miyata et al. |
| 5,383,924 | A | 1/1995 | Brehier |
| 5,489,294 | A | 2/1996 | McVenes et al. |
| 5,527,358 | A * | 6/1996 | Mehmanesh et al. ......... 607/129 |
| 5,549,615 | A | 8/1996 | Hocherl et al. |
| 5,647,857 | A | 7/1997 | Anderson et al. |
| 5,649,975 | A | 7/1997 | Lindegren et al. |
| 5,683,405 | A | 11/1997 | Yacoubian et al. |
| 5,735,891 | A | 4/1998 | White |
| 5,772,693 | A | 6/1998 | Brownlee |
| 5,775,328 | A | 7/1998 | Lowe et al. |
| 5,983,142 | A | 11/1999 | Bridges |
| 6,216,042 | B1 | 4/2001 | Robertson |
| 6,231,514 | B1 | 5/2001 | Lowe et al. |
| 6,256,543 | B1 | 7/2001 | Spence |
| 6,330,481 | B1 * | 12/2001 | Van Wijk et al. ............ 607/129 |
| 6,334,873 | B1 | 1/2002 | Lane et al. |
| 6,532,387 | B1 | 3/2003 | Marchitto et al. |
| 6,562,049 | B1 | 5/2003 | Norlander et al. |
| 2006/0100683 | A1 | 5/2006 | Yacoubian |

FOREIGN PATENT DOCUMENTS

| | | |
|---|---|---|
| JP | 2001-087397 A | 4/2001 |
| WO | WO 93/09840 A1 | 5/1993 |
| WO | WO-9956692 | 11/1999 |
| WO | WO-2004043518 | 5/2004 |

OTHER PUBLICATIONS

Sherbeeny, M "Needles, Sutures, and Knots: Part I: Needles", *ASJOG*, vol. 1, (Jan. 2004),29-30.
Yacoubian, et al., "Notification of transmittal of the international search report and the written opinion of the ISA", (Jan. 14, 2008).
Canadian Intellectual Property Office, Notice of Allowance mailed Jun. 10, 2010 in Canadian Patent Application No. 2,505,133, 1 page.
United States Patent and Trademark Office, Notice of Allowance mailed Jun. 18, 2009 in U.S. Appl. No. 10/534,309, 4 pages.
United States Patent and Trademark Office, Final Office Action mailed Mar. 19, 2009 in U.S. Appl. No. 10/534,309, 10 pages.
Israel Patent Office, Office Action mailed Nov. 24, 2008 in Israeli Patent Application No. 168455, 2 pages.
United States Patent and Trademark Office, Office Action mailed May 28, 2008 in U.S. Appl. No. 10/534,309, 10 pages.
Canadian Intellectual Property Office, Office Action mailed Apr. 18, 2008 in Canadian Patent Application No. 2,505,133, 4 pages.
WIPO, International Search Report mailed May 24, 2004 in International Patent Application No. PCT/US2003/035875, 4 pages.
WIPO, International Preliminary Examination Report mailed Jan. 25, 2005 in International Patent Application No. PCT/US2003/035875, 11 pages.

* cited by examiner

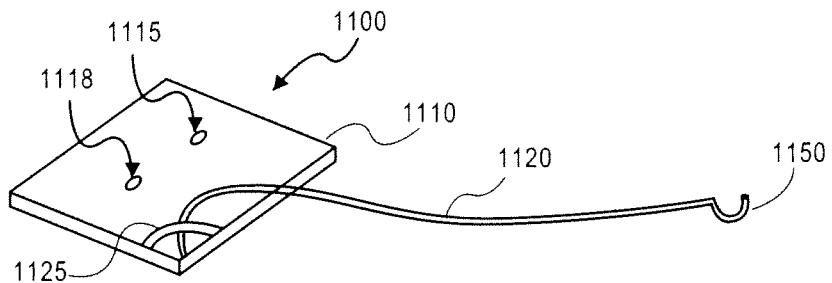
FIG. 11
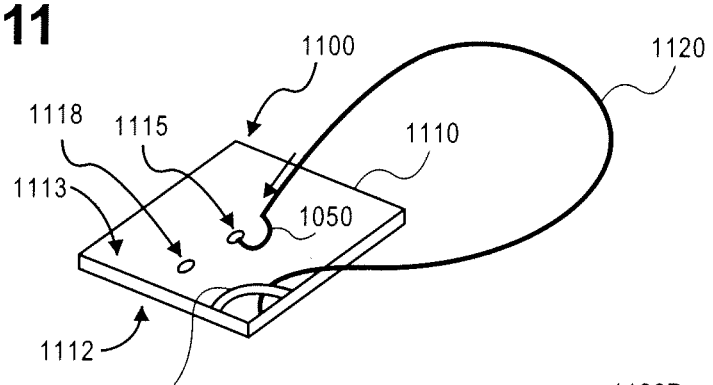
FIG. 12
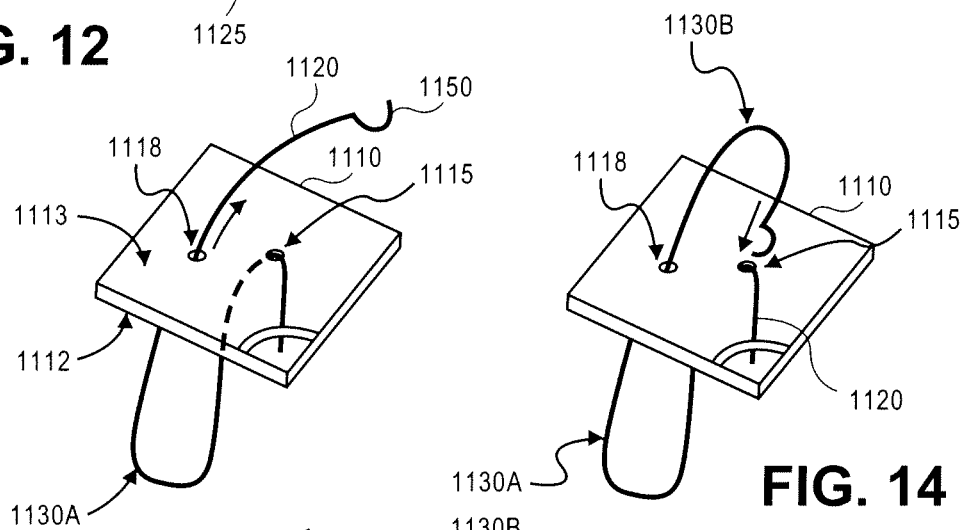
FIG. 13
FIG. 14
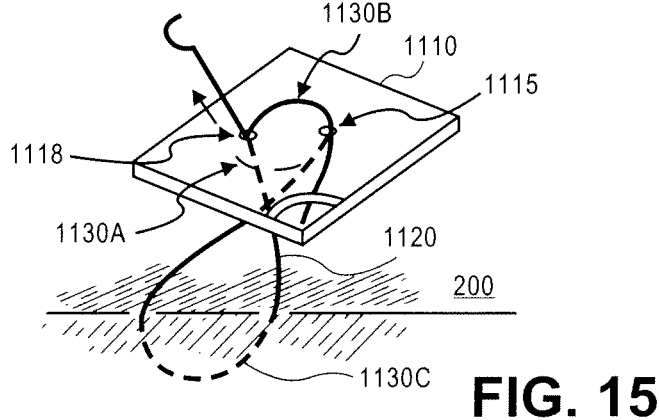
FIG. 15

HEART WIRE

CROSS-REFERENCE TO RELATED APPLICATION

This application claims the benefit of the earlier filing date of co-pending U.S. Provisional Patent Application No. 60/822,563, filed Aug. 16, 2006, and incorporated herein by reference.

FIELD

Epicardial heart wires (also called a temporary myocardial pacing wires or stimulation leads) and methods of attaching the same.

BACKGROUND

A heart wire or heart wires are typically positioned epicardially to the myocardium and stitched or passed through a myocardial tunnel. Typically, they stay in a patient between one and seven days, usually for one to two days, and preferably less than seven days, after open-heart surgery. Before a patient is released from a hospital, the heart wire or wires are pulled out of the myocardium. Since a myocardium is a moving muscle, a heart wire connected to the myocardium must be able to move. Thus, a heart wire is intended, though only temporarily, to be fixed on a moving muscle. Since the muscle can move, there is a concern that the heart wire can become dislodged. To address the concern for retention of a heart wire in myocardial tissue, heart wires have been designed that have irregular or three-dimensional structures, such as zigzagged and/or tines of prolene material. When these structures are pulled out when no longer needed, the myocardial tissue may be injured or disturbed and there is a risk of bleeding. The risk of bleeding is particularly relevant for patients that may be prescribed blood thinners at the time where the amount of bleeding may be increased.

One effort to reduce bleeding at the myocardium associated with removal of a heart wire is to place a conductive portion of the heart wire under a pledget so that the heart wire is in contact with a surface of the myocardium. Pledgets are relatively small biocompatible cotton, Teflon or similar material that may be stitched to the heart by fine prolene sutures to repair or close the heart. These pledgets are permanently sutured to the myocardium. One technique of placing a heart wire is to place a heart wire with an electrically conductive end under a pledget and suture the pledget to the myocardium. The heart wire has an irregular three-dimensional end (e.g., a hook, zigzag or tines or prolene material) that serves to retain the heart wire under the pledget. When the heart wire is removed, the heart wire including the irregular three-dimensional structured end may be removed without damaging the myocardium.

One concern of placing a conductive portion of a heart wire on a surface of the myocardium is whether the heart wire is placed over adequate (e.g., healthy) tissue, or scar tissue or fat. If the heart wire is placed over scar tissue or fat, there is a risk that attempts to pace the heart through this heart wire will fail.

Typically, when a heart wire is placed in a patient, a physician will put an extra length of wire in the form of a loop inside the patient to increase the freedom of movement of the wire when the myocardium moves (e.g., when the heart is beating). In addition to the risk of injury or disturbance to the myocardium when a heart wire is removed, there is a risk that the loop of wire being pulled out may catch a vein or other structure. This risk is especially dangerous when a loop of wire becomes tangled around a vein graft, which may moreover have metallic clips applied at its branching sites.

One technique to reduce the additional length of a heart wire (e.g., extra looping length) is to connect the heart wire to the pericardium. To expose a heart of a patient, a physician must open the pericardium. Opening the pericardium requires a longitudinal cut therethrough with the sides of the pericardium that have been cut remaining in a relatively fixed position relative to one another. A physician then connects one or more heart wires (e.g., a negative lead and a ground wire). The heart wire or wires may then be connected to the pericardium. Because the pericardium is close to the chest walls of the patient, the need for an extra length or loop of wire is reduced. Another option to reduce the length of additional wire retained in a patient is to use a chest tube. Chest tubes are commonly used to evacuate blood from the mediastinum (interpleural space) after open-heart surgery. They are also used to evacuate air and blood from the thoracic cavity after thoracotomy for lung or pleural surgery. A chest tube typically stays in the mediastinum after heart surgery for one to three days depending on the amount of post-operative drainage present. Following open-heart surgery, chest tubes are typically located very close to the heart and extend out of a patient's chest through the skin and are fixed with a suture in that location. A commonly-used type of chest tube is a plastic tube made of biocompatible synthetic rubber, which is between 20 and 40 centimeters long, and has holes at a distal section. The holes allow excess blood to enter the chest tube. The chest tube is typically connected to a vacuum machine.

In one known design, a heart wire is connected to a chest tube and inserted at the same time as the chest tube. After insertion of the chest tube, the heart wire can be partially disconnected from the chest tube if necessary to reach the myocardium. An advantage of this combination is that when it is time for the chest tube and the heart wire to be removed, they can be removed together. Another advantage is that the heart wire follows a direct path to the heart, so there are no additional loops of wire needed. Thus the risk of a heart wire being tangled on a vein is reduced. In bipolar heart wire configurations, another advantage is that a chest tube can incorporate the ground pole associated with the heart wire leads.

BRIEF DESCRIPTION OF THE DRAWINGS

Features, aspects, and advantages of embodiments will become more thoroughly apparent from the following detailed description, appended claims, and accompanying drawings in which:

FIG. 11 shows a top side perspective view an embodiment of an apparatus including an anchor connected to a pledget.

FIG. 12 shows the apparatus of FIG. 11 with the hook at the end of the anchor being looped and placed into an opening through the pledget.

FIG. 13 shows the apparatus of FIG. 12 with the anchor on a loop below the pledget and the end of the anchor coming through a second hole through the pledget.

FIG. 14 shows the apparatus of FIG. 13 where the anchor has another loop over the pledget and the end of the anchor is aligned with the first hole through the pledget.

FIG. 15 shows the apparatus of FIG. 14 where the anchor forms a loop in myocardial tissue and is advanced through the second hole through the pledget.

DETAILED DESCRIPTION

Figure 1:
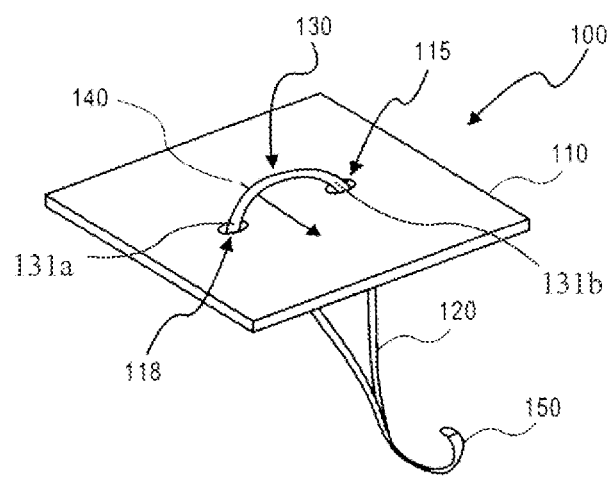
FIG. 1 shows a top side perspective view of an apparatus including a pledget having an anchor disposed therethrough in a manner to form a loop over a surface of the pledget.

FIG. 1 shows an embodiment of an apparatus suitable, in one embodiment, for securing a heart wire to myocardial tissue. Referring to FIG. 1, apparatus 100 includes pledget 110 and anchor 120. In one embodiment, pledget 110 is a flexible material of, for example, cotton, Teflon, or other biocompatible synthetic or natural material that may be suitable for being stitched to myocardial tissue and permanently remain attached. A representative example of a size of pledget 110 is, for example, on the order of ⅜ inches (in)×⅜ in×⅙ in. Other dimensions may also be used as will be clear from the discussion that follows. In the embodiment described with reference to FIG. 1, pledget 110 includes opening 115 and opening 118 each through opposing surfaces of the pledget. The openings may be pre-formed or created by disposing legs 131a and 131b of an anchor 120 therethrough as described below (e.g., by tearing or poking through the pledget).

Disposed through opening 115 and opening 118 on pledget 110 is anchor 120. In one embodiment, anchor 120 is a conductive material in the form of a wire having, for example, a round or rectangular (e.g., square) cross section. Anchor 120 may be formed of a conductive material such as stainless steel or titanium and, as a wire, may have a diameter of, for example, 0.2 millimeters (mm) or greater (e.g., 0.5 mm, 0.6 mm, 0.8 mm, etc.). A suitable wire size is, for example, one that can be manipulated by a physician into and out of myocardial tissue using a needle holder. As shown in FIG. 1, anchor 120 is disposed through opening 115 and opening 118 of pledget 110 such that anchor 120 forms loop 130 over a surface (a superior surface as viewed) of pledget 110. Loop 130 provides opening 140 for a heart wire to be placed between loop 130 and a surface of pledget 110. In this manner, a heart wire may be connected to apparatus 100 by securing the heart wire with loop 130 (e.g., by tightening loop 130 against the heart wire).

As a wire, for example, respective ends of anchor 120 of apparatus 100 may each be inserted through openings 115 and 118, respectively, and brought together beyond an opposing surface of pledget 110. FIG. 1 shows an end of anchor 120 (opposite loop 130) as a single end having a structure 150 such as a straight or curved needle (e.g., thoracic or Keith-type needle) that is capable of puncturing myocardial tissue. In one embodiment, where anchor 120 is a wire, the single end of structure 150 is formed of the combined ends of anchor 120. In another embodiment, the single end of structure 150 is formed of a first end of anchor 120 with a second end of the wire connecting to the first end of a point above structure 150. A length dimension of anchor 120 (from loop 130 to an end of structure 150) should be sufficient so that a length of anchor 120 may be positioned in and pulled through myocardial tissue to leave loop 130 over pledget 110 and allowing a distal portion to be clipped with standard clips used in surgery (e.g., "silver clips"). As will be clear later, excess length is suitable as any excess may be removed in a procedure to secure a heart wire.

Figure 2:
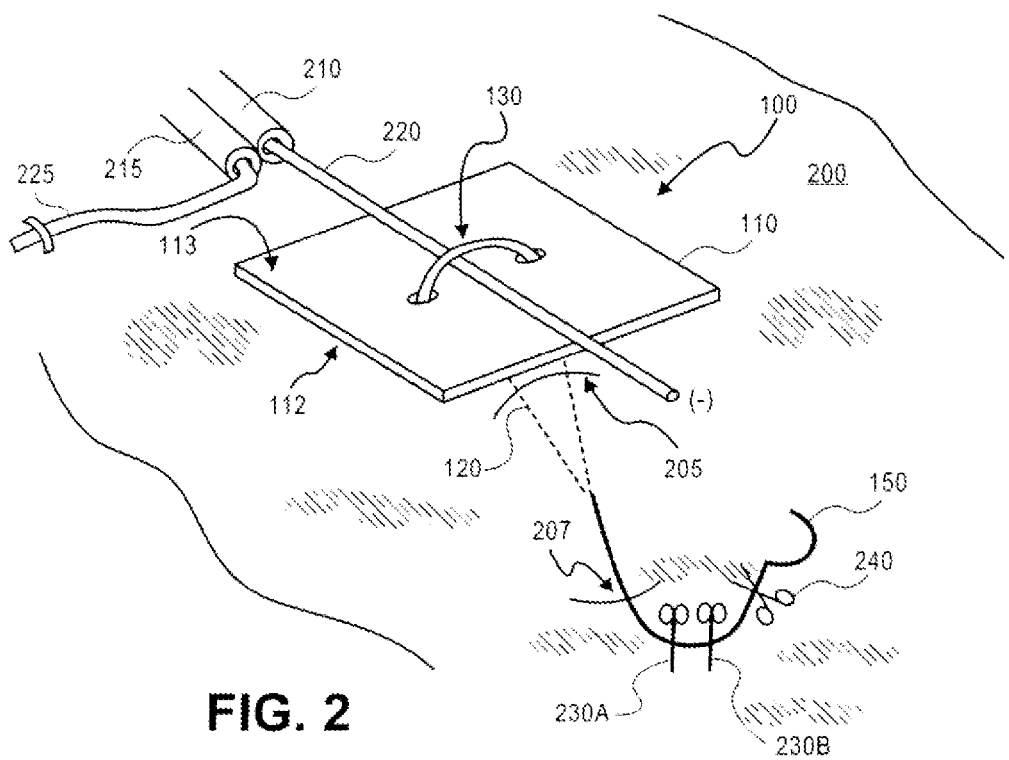
FIG. 2 shows the apparatus of FIG. 1 with the pledget affixed to myocardial tissue by the anchor and a heart wire disposed on a superior (exposed) surface of the pledget between a loop of the anchor and the pledget.

FIG. 2 shows the apparatus of FIG. 1 connected to myocardial tissue. Referring to FIG. 2, apparatus 100 is positioned such that pledget 110 lies on a surface of myocardial tissue 200. As viewed, pledget 110 includes surface 112 in contact with a surface of myocardial tissue 200 and opposite surface 113 exposed (surface 113 is shown as the superior or top surface). As illustrated, anchor 120 is disposed into myocardial tissue 200 to a sufficient depth to contact healthy (e.g., non-infarcted or healthy) tissue. Representatively, anchor 120 may be manipulated by a physician's (e.g., surgeon's) needle holder into myocardial tissue and then removed such that point 205 where anchor 120 is inserted is different from point 207 where anchor 120 is removed from myocardial tissue. Thus, anchor 120 is inserted into myocardial tissue to catch a portion of healthy myocardial tissue and leave an end of anchor 120 exposed. In this embodiment, if the wire is placed over scar tissue, the anchor provides good conductivity through myocardial tissue.

Following insertion of anchor 120 into myocardial tissue 200, heart wire 210 may be positioned on or adjacent surface 113 of pledget 110. Heart wire 210 may be a commercially available heart wire including one with an irregular structure (e.g., zigzag, tine, etc.) and/or a needle at one end. Heart wire 210 may be an insulated wire that has conductive portion 220 exposed (e.g., insulation removed). In this manner, conductive portion 220 of heart wire 210 is in physical contact with loop 130 of anchor 120. Portion 220 of an electrically conductive material and loop 130 also of electrically conductive material are similarly in electrical contact. Portion 220 serves, in one embodiment, as a negative pole. In the example shown in FIG. 2, heart wire 215 is adjacent and possibly connected to heart wire 210 (e.g., insulated portions of the wires connected by an adhesive and/or thermal bond). Heart wire 215 includes conductive portion 225 that can serve as a positive pole. FIG. 2 shows portion 225 connected to the heart, not necessarily to myocardial tissue, by a suture.

Having placed portion 220 of heart wire 210 between loop 130 of anchor 120 and surface 113 of pledget 110, a distal end of anchor 120 may be pulled tight by applying a pulling force at structure 150 (a force in a direction away from myocardial tissue 200 and pledget 110) to establish good contact between loop 130 of anchor 120 and portion 220 of heart wire 210. Following the establishment of good contact, one or more clips (clip 230A and clip 230B shown) such as standard clips used in surgery (e.g., "silver clips") may be affixed near a distal end of anchor 120 and structure 150 of anchor 120 may be cut (illustrated by scissors 240).

As illustrated in FIG. 2, conductive portion 220 of heart wire 210 is not placed into myocardial tissue 200. Instead, anchor 120 is placed in myocardial tissue 200. Conductive portion 220, is positioned between pledget 110 and loop 130 of anchor 120. If heart wire 210 includes an irregular structure and/or needle at one end (an end distal to loop 130 once placed), the irregular structure and/or needle may be removed (e.g., via scissors). Alternatively, if the heart wire includes both an irregular structure and a needle at its end, only the needle may be removed as described with reference to FIG. 22 herein. Regardless of a configuration of heart wire 210, the heart wire need not be inserted into myocardial tissue. Accordingly, at a time for removal of heart wire 210, the heart wire may be removed without causing trauma to myocardial tissue. In addition, should conductive portion 220 inadvertently be displaced from a position between anchor 130 and pledget 110, conductive portion 220 may be reinserted without causing any trauma to myocardial tissue 200 rather than asking for a new set of pacing wires (which is costly) by using a suture connecting loop 130 to heart wire 220.

Figure 3:
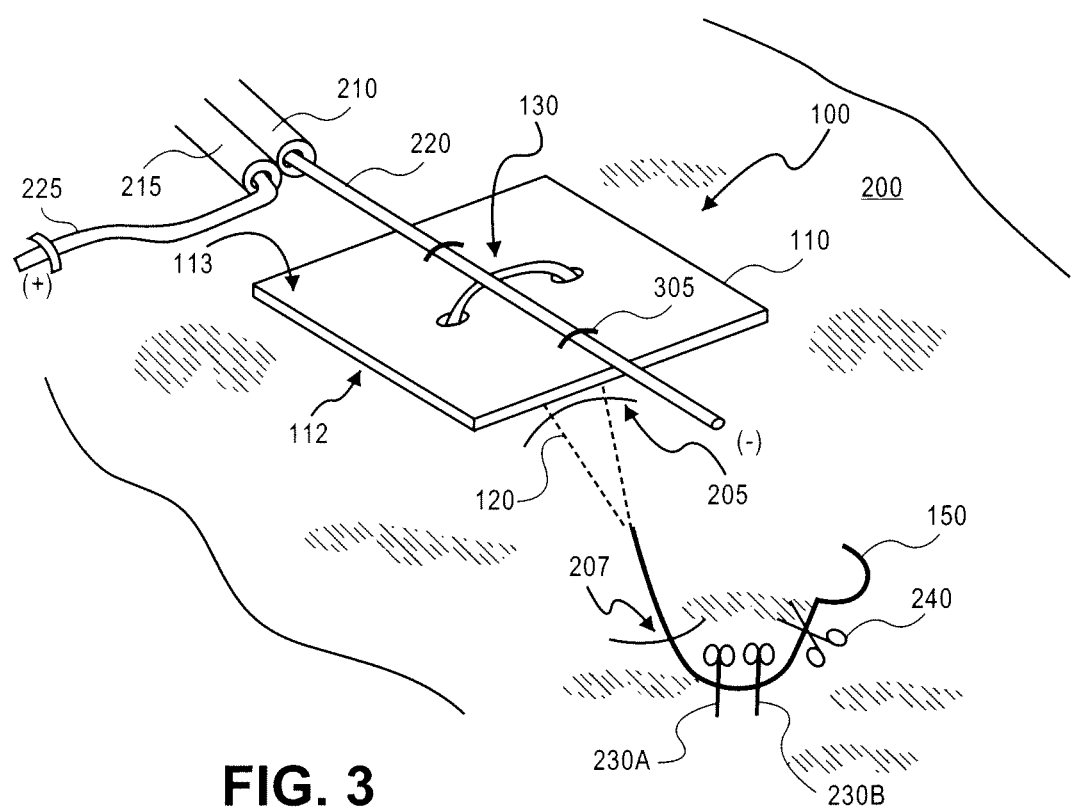
FIG. 3 shows the apparatus of FIG. 1 with the pledget affixed to myocardial tissue by the anchor and a heart wire disposed on a superior (exposed) surface of the pledget on the loop of the anchor.

FIG. 3 shows another technique for electrically connecting conductive portion 220 to anchor 120. This connection technique could be used where conductive portion 220 is inadvertently displaced from a position between anchor 130 and pledget 110. Rather than removing anchor 120, conductive portion 220 is placed over loop 130 of anchor 130 so that conductive portion 220 and loop 130 make electrical contact.

Conductive portion 220 is fixed in this position by one or more sutures 305 through pledget 110.

Figure 4:
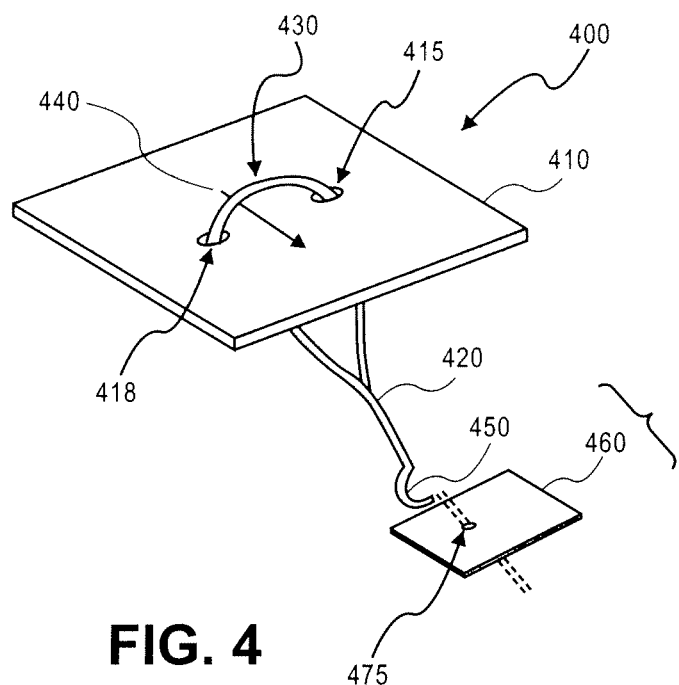
FIG. 4 shows a top side perspective view of another embodiment of an apparatus including a pledget and anchor system including a pledget having an anchor disposed therethrough in a manner to form a loop over a surface the pledget and a second pledget on a distal portion of the anchor.

In the above embodiment, a distal portion of anchor 120 is secured in place on myocardial tissue 200 with clips in contact with myocardial tissue 200. In another embodiment, a distal portion of an anchor may be inserted through a pledget such that any clips to secure the anchor are not in direct contact with myocardial tissue but are separated from the myocardial tissue by pledgets. FIG. 4 shows an embodiment of an apparatus including pledget 410 and anchor 420. Pledget 410 and anchor 420 may be similar to pledget 110 and anchor 120 described above with reference to FIG. 1. Thus, pledget 410 includes opening 415 and opening 418 through a surface of the pledget. Anchor 420 is disposed through the pledget such that loop 430 is disposed over a surface of the pledget (a top or superior surface as viewed) and defines opening 440 between loop 430 and a surface of pledget 410. A heart wire may be positioned through opening 440.

Anchor 420 of apparatus 400 of FIG. 4 also includes at a distal end structure 450 that is capable of puncturing myocardial tissue. Apparatus 400 also includes pledget 460 that may have length and width dimensions similar to dimensions of pledget 410 or, in one embodiment, have length and width dimensions smaller than dimensions of pledget 410. Pledget 460 includes opening 470 through opposing surfaces thereof. Opening 470 forms an opening that structure 450 of anchor 420 may be inserted through pledget 460. Alternatively, pledget 460 need not include an opening and opening 470 may be formed by pushing structure 450 through the pledget. In such instance, an area for opening 470 may optionally be marked with, for example, ink or dye.

Figure 5:
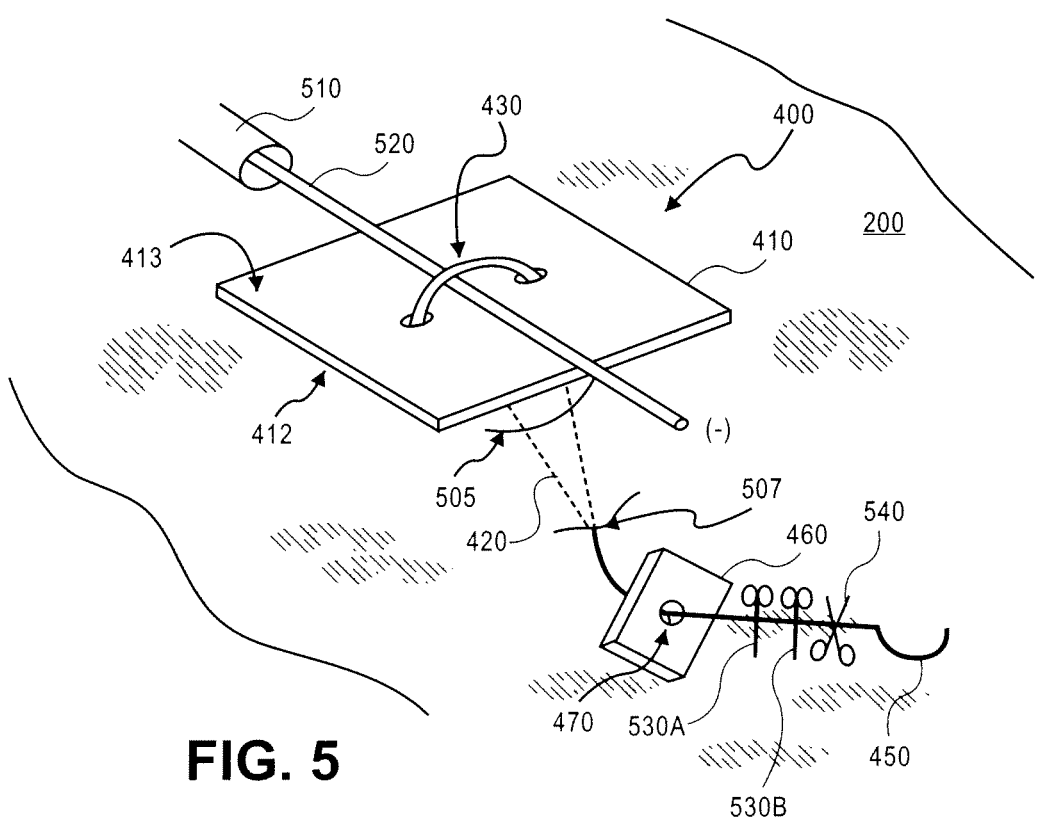
FIG. 5 shows a perspective view of the apparatus of FIG. 4 affixed to myocardial tissue using the anchor and a heart wire positioned on an exposed surface of the pledget between the pledget and the loop of the anchor.

FIG. 5 shows apparatus 400 positioned on myocardial tissue 200. As viewed, surface 412 of pledget 410 is in contact with a surface of myocardial tissue 200 while surface 413 opposite surface 412 is exposed. FIG. 5 shows anchor 420 disposed into myocardial tissue 200 at site 505 and removed from myocardial tissue 200 at site 507. In this manner, anchor 420 has a position that is in myocardial tissue 200.

Once anchor 420 is engaged with myocardial tissue 200, heart wire 510 may be inserted under loop 430 of anchor 420 such that heart wire 510, conductive portion 520 of heart wire 510, lies between loop 430 of anchor 420 and surface 413 of pledget 410. Once conductive portion 520 is positioned under loop 430 of anchor 420, anchor 420 may be tightened by a pulling force on a distal portion thereof. By pulling a distal portion of anchor 420 away from myocardial tissue 200, loop 430 is pulled toward myocardial tissue and in contact with conductive portion 520 of heart wire 510 to establish electrical contact between anchor 420 and conductive portion 520.

FIG. 5 also shows pledget 460 on myocardial tissue 200. In this embodiment, a distal portion of anchor 420 including structure 450 is advanced through opening 470 in pledget 460. Pledget 460 is then placed in contact with myocardial tissue 200. Anchor 420 is then secured by one or more clips (clips 530A and clip 530B as shown) applied on a non-tissue side of pledget 460. Following securing of anchor 420 with clips, a distal end of anchor 420 including structure 450 may removed such as by cutting or snipping with scissors 540.

Figure 6:
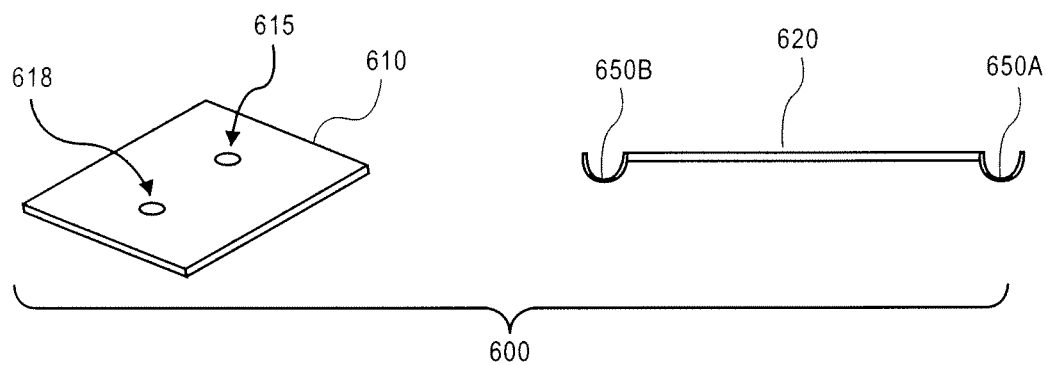
FIG. 6 shows a perspective view of an apparatus or kit including a pledget and anchor wherein the anchor is a length of conductive wire having structures at each end capable of puncturing myocardial tissue.

In the embodiments described with reference to FIGS. 1-5, an apparatus includes an anchor that defines a loop at a proximal end and a second or distal end is a single structure (e.g., structure 150 or structure 450) that is capable of puncturing myocardial tissue. One way such an anchor may be formed is a suitable length of wire inserted through openings in a pledget and brought together beyond a second surface of the pledget to define a single end. FIG. 6 shows apparatus 600 that includes pledget 610 that may be similar in dimensions to pledget 110 as described with reference to FIG. 1. Pledget 610 includes opening 615 and opening 618 through the pledget to accommodate an anchor. These may be pre-existing openings or marked areas for openings. In other embodiments, no openings or marked areas exist allowing a surgeon or the surgeon's assistant to make the openings with, for example, an anchor. Apparatus 600 also includes an anchor 620 having first end 650A and second end 650B. End 650A may be inserted through opening 615 of pledget 610 while end 650B is inserted through opening 618. In this manner, anchor 620 may form a loop on an exposed surface of pledge 610.

Figure 7:
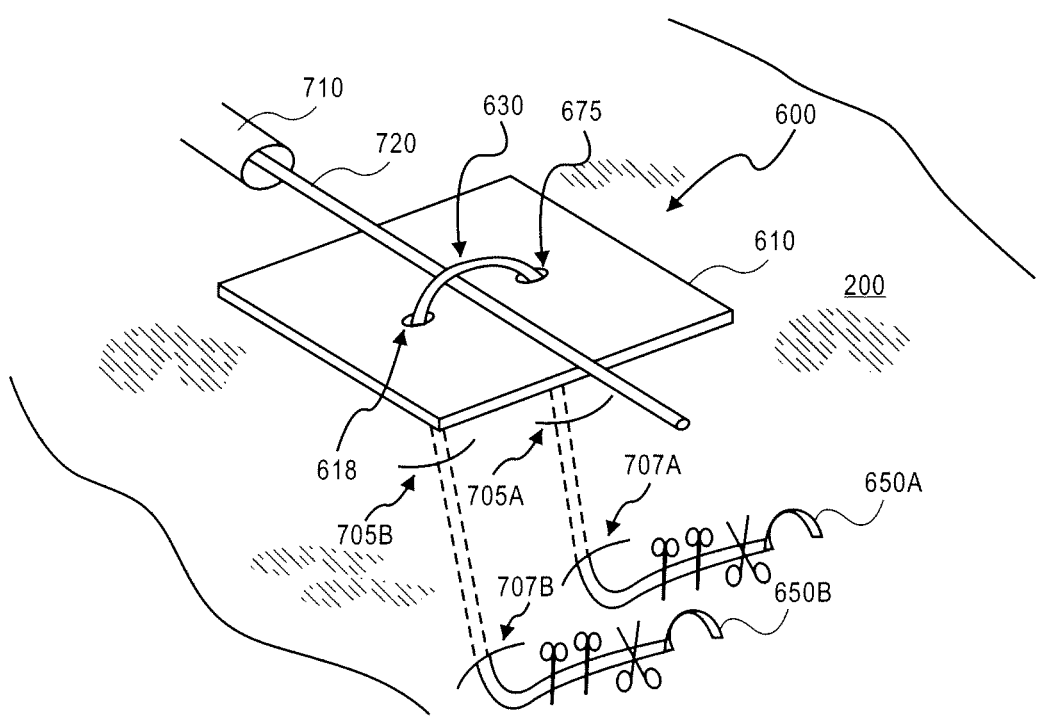
FIG. 7 shows the apparatus or kit of FIG. 6 with the anchor disposed through a surface of the pledget and into myocardial tissue and a heart wire on an exposed surface of the pledget between the pledget and the anchor.

FIG. 7 shows the apparatus of FIG. 6 connected to myocardial tissue. FIG. 7 shows pledget 610 of apparatus 600 having a surface in contact with myocardial tissue 200. FIG. 7 also shows anchor 620 of apparatus 600 disposed through pledget 610. Representatively, first end 650A is placed through opening 615 in pledget 610 and second end 650B is placed through opening 618. Each end of anchor 620 is introduced into myocardial tissue and engages myocardial tissue. FIG. 7 shows structure 650A inserted into myocardial tissue 200 at point 705A and retrieved from myocardial tissue 200 at point 707A. Similarly, second end 650B is inserted into myocardial tissue 200 at point 705B and retrieved from myocardial tissue 200 at point 707B. Following the engagement of myocardial tissue by anchor 620, a heart wire may be engaged by apparatus 600. FIG. 7 shows heart wire 710 having conductive portion 720 (e.g., a negative pole) inserted under loop 630 of apparatus 600. Following the placement of heart wire 710, anchor 620 may be tightened by applying a pulling force to one or both of structure 650A and structure 650B away from myocardial tissue 200. Applying such a pulling force forces loop 630 of anchor 620 against portion 720 of heart wire 710 to establish physical and electrical contact between anchor 620 and the heart wire. Once good contact has been made and heart wire 710 is secured to apparatus 600, anchor 620 may be secured to myocardial tissue 200 by applying clips to each distal portion. Distal ends including structure 650A and 650B may then be removed such as by clipping or cutting. In an alternative embodiment, a secondary pledget may be placed on each of the distal ends of the anchor and clips applied on a distal side of each secondary pledget or a single secondary pledget.

Figure 8:
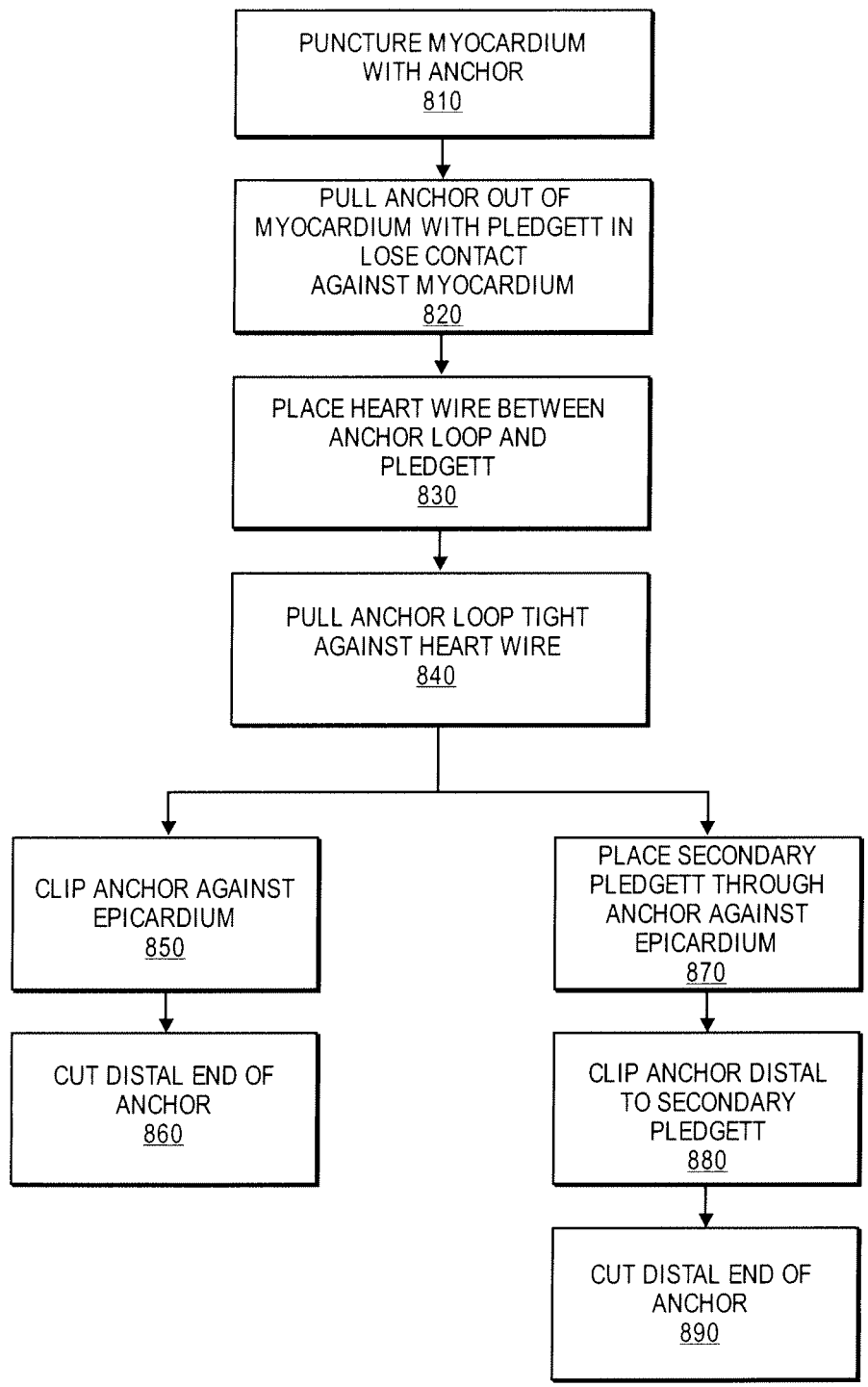
FIG. 8 describes a flow chart for methods of securing a heart wire to myocardial tissue.

FIG. 8 shows a flowchart of attaching a heart wire to myocardial tissue such as described above with reference to FIGS. 2, 5 and 7. Referring to FIG. 8, one method includes puncturing a myocardium with an anchor of an apparatus (block 810). For example, apparatus 100 of FIG. 1 includes anchor 120 through pledget 110. Anchor 120 includes structure 150 at an end that is capable of puncturing myocardial tissue. In FIG. 6, apparatus 600 includes anchor 620 that has end 650A and 650B. In this embodiment, each of structure 650A and structure 650B would puncture myocardial tissue. It is appreciated that prior to puncturing myocardial tissue with anchor 620, structures 650A and structure 650B would be placed through openings in pledget 610 as described above.

Referring again to FIG. 8, following puncturing myocardial tissue with an anchor of an apparatus, the anchor may be pulled through and out of myocardial tissue such that a pledget of the apparatus is disposed against myocardial tissue (block 820). By exerting a force on an anchor into myocardial tissue and positioning a pledget against the myocardial tissue, a loop of the anchor will be formed over a surface of the pledget.

Following placement of a pledget against myocardial tissue, a conductive potion of a heart wire may be inserted between a loop of the anchor over the pledget and the pledget (block 830). A pulling force may then be applied to a distal end of the anchor in a direction away from the myocardial tissue and the pledget so as to pull the loop of the anchor tight against the heart wire (block 840).

In one embodiment, once the anchor loop is secured tight against a heart wire to establish physical and electrical contact between the anchor and the heart wire, a distal portion of the anchor may be clipped against the myocardium or epicardium (block 850). A distal end of the anchor may then be cut (block 860). In another embodiment, once an anchor is pulled tight against a heart wire, a distal end of the anchor may be inserted through a secondary pledget and the pledget placed against the myocardium or epicardium (block 870). Following placement of a secondary pledget, the anchor may be clipped so that the clipping occurs between the tissue and the pledget (distal to the secondary pledget (block 880). A distal end of the anchor may then be cut (block 890).

In one embodiment of a pacing operation, two wires may be necessary, where one wire is, for example, a negative lead and the other wire is connected to ground. In such a configuration, the negative lead may be connected as described in FIGS. 1-8 and the ground lead connected to epicardium (as described with reference to FIG. 2). Alternatively, subcutaneous tissue can be used as a ground or the skin surface with, for example, an electrode as described with reference to FIG. 22.

Figure 9:
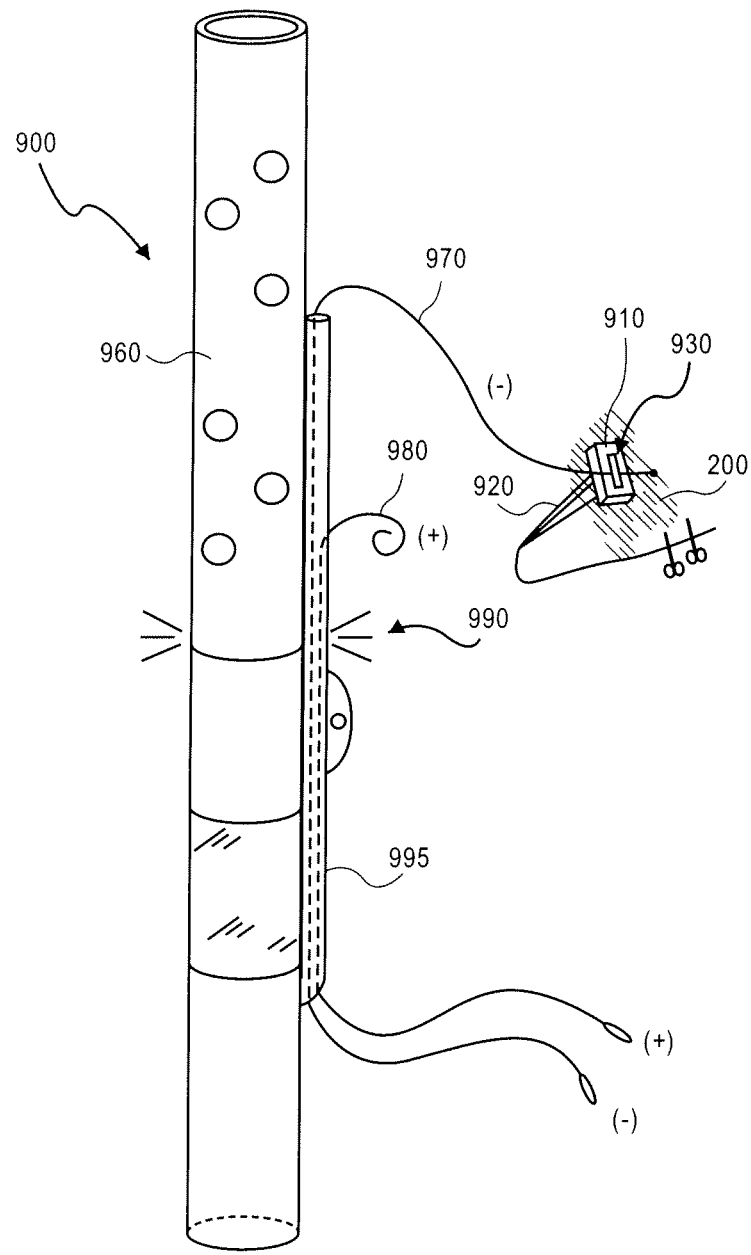
FIG. 9 shows an embodiment of a heart wire connected to a chest tube and electrically connected to myocardial tissue similar to the connection described with reference to FIG. 2.

FIG. 9 shows a system wherein two heart wires are connected to a chest tube. Referring to FIG. 9, system 900 includes pledget 910 having conductive anchor 930 disposed through a surface thereof similar to, for example, the embodiment described with reference to FIG. 1. System 900 also includes heart wire 970 and heart wire 980. Each of heart wire 970 and heart wire 980 are connected to chest tube 960. Heart wire 970 extends to a distal end of chest tube 960 and heart wire 980 extends a length such as would be approximately into the chest just past skin level 990. In this embodiment, heart wire 980 is used for grounding and would be in contact with subcutaneous tissue and beyond, without necessarily being fixed to such tissue.

Heart wire 970 that is a negative lead is secured to an elongated structure on chest tube 960. The elongated structure may be a groove or channel (not shown) formed in an outside portion of chest tube 960 and covered there by silastic or other thin film (not shown). Alternatively, heart wires 970 and 980 may be disposed through a conduit, such as conduit 995 on a side of chest tube 960.

During surgery to place a heart wire (heart wire 970), heart wire 970 may be pulled away from chest tube 960 and moved to a selected position on myocardium 200. Heart wire 970 may be attached between anchor 930 and pledget 910 to make physical and electrical contact with anchor 930.

In one embodiment, heart wire 970 is a negative lead that may be placed on an atrium for atrial pacing. In another embodiment, heart wire 970 may be placed on a ventricle for ventricle pacing. In either case, heart wire 970 is connected to a negative pole of a pacemaker. Heart wire 980 is a positive lead and is connected to a positive pole of a pacemaker. As such, only heart wire 970 needs to enter the chest cavity.

Figure 10:
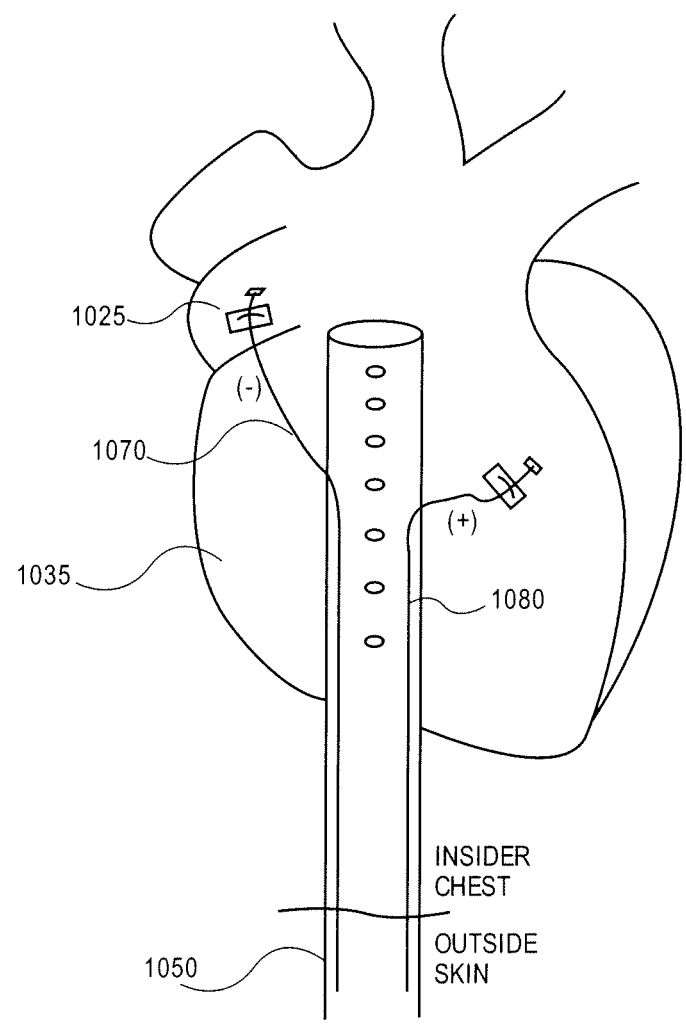
FIG. 10 shows a perspective view of a front side of heart having a heart wire secured to a pledget on a right ventricle of the heart and a second heart wire secured to a pledget on a right atrium of the heart.

FIG. 10 shows an embodiment of connecting multiple heart wires. By connecting a negative lead to an atrium and a positive lead to a ventricle, atrial-ventricular (AV) sequential pacing becomes possible. AV pacing provides increased cardiac output over ventricular pacing. AV pacing mimics the normal contraction of a heart. FIG. 10 shows an AV pacing configuration where heart wire 1070 that is a negative lead is attached to right atrium 1025 through an apparatus such as described above in relation to the embodiments presented in FIGS. 1-7. FIG. 10 also shows heart wire 1080 that is a positive lead connected to ventricle 1035, again, by, for example, an apparatus such as described in the embodiments presented in FIGS. 1-7.

FIG. 10 shows heart wire 1070 and heart wire 1080 coupled to an atrium and a ventricle of a heart, respectively. In one embodiment, heart wire 1070 and 1080 may further be connected to chest tube 1050 and be inserted via the chest tube as described, for example, with respect to FIG. 9. In another embodiment, two chest tubes/heart wire combinations similar to that described with respect to FIG. 9 may be used for respectively pacing an atrium and a ventricle. In such an arrangement, the shorter ground wires on the respective chest tubes would not be used. Alternatively, two chest tubes may be used where each chest tube contains only one heart wire. Here, atrial, ventricular and AV sequential pacing will be possible if the need arises.

FIGS. 11-15 show another embodiment of an apparatus and configurations of the apparatus to provide a conductive anchor to myocardial tissue for use in myocardial pacing.

FIG. 11 shows apparatus 1100 including pledget 1110 and anchor 1120. Anchor 1120 is clipped at one end to pledget 1110 through clip 1125. A second end of anchor 1120 includes structure 1150 capable of puncturing myocardial tissue. Anchor 1120 is, for example, a wire that has a length suitable to be inserted through pledget 1110 multiple times to form multiple loops as well as a loop into myocardial tissue. A suitable length is on the order of, for example, 20 centimeters or more.

Referring to FIG. 12, as a first act to configure apparatus 1100 for connecting to myocardial tissue and a heart wire, a distal end of anchor 1120 is inserted through opening 1115 in pledget 1110. A length of anchor 1120 is pulled through opening 1115. Opening 1115 extends through surface 1113 of pledget 1110 (a superior or exposed surface) and surface 1112 that is intended to be in contact with myocardial tissue.

FIG. 13 shows the structure of FIG. 12 following the formation of a first loop of anchor 1120. As viewed, a distal end of anchor 1120 is pulled through opening 1115 and then advanced from surface 1112 of pledget 1110 into opening 1118 to form loop 1130A on an underside of pledget as viewed (on a side corresponding to surface 1112 of pledget 1110).

FIG. 14 shows the structure of FIG. 13 following the formation of a second loop for anchor 1120. Referring to FIG. 14, a portion of anchor 1120 is pulled through opening 1118 and then a distal end of anchor 1120 is inserted through opening 1115 and a length of the anchor pulled through the opening. FIG. 14 shows the formation of loop 1130B on a superior surface of pledget 1110.

FIG. 15 shows the structure of FIG. 14 following the connection of anchor 1120 with myocardial tissue. Referring to FIG. 15, anchor 1120 is inserted into myocardial tissue 200 in a manner similar to that described above, for example, with respect to FIG. 2 or 5 in the accompanying text. As shown in FIG. 15, anchor 1120 is disposed into myocardial tissue 200 and out of myocardial tissue 200 to form loop 1130C in myocardial tissue 200. A distal end of anchor 1120 is then inserted through opening 1118 and pulled through pledget 1110 after optionally placing a heart wire between epicardium and loop 1130A so that a conductive portion of the heart wire will be in electrical contact with loop 1130A.

Figure 16:
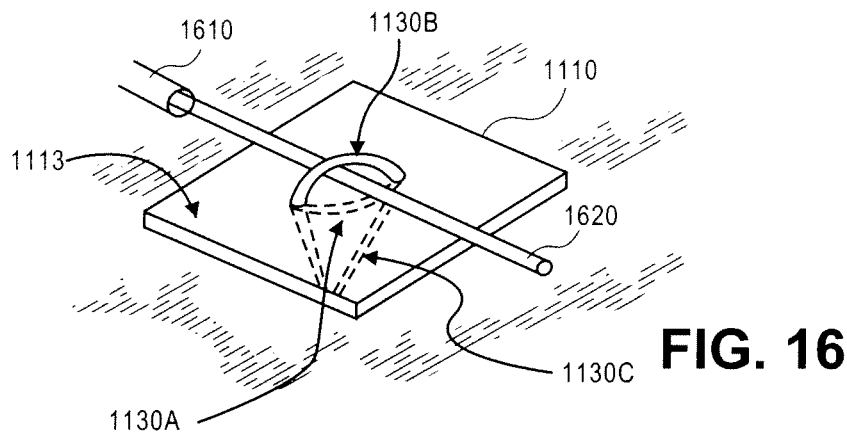
FIG. 16 shows the apparatus of FIG. 15 where a heart wire is secured to the pledget through a loop over a surface of the pledget and the heart wire is between the pledget and the loop over a surface of the pledget.
Figure 17:
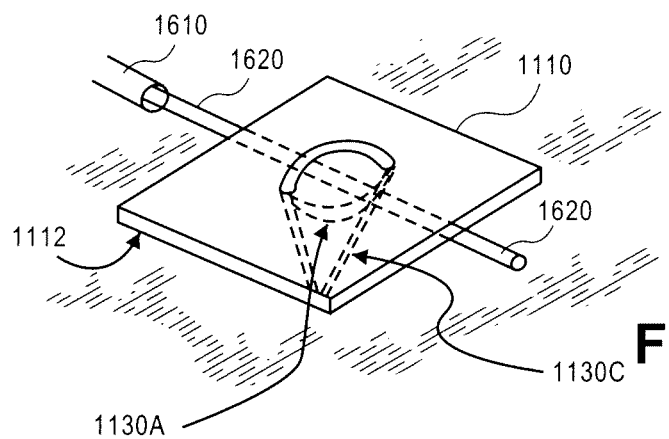
FIG. 17 shows the apparatus of FIG. 15 in another embodiment wherein a heart wire is secured to the pledget through a loop under the pledget wherein the heart wire is disposed between the pledget and the anchor.
Figure 18:
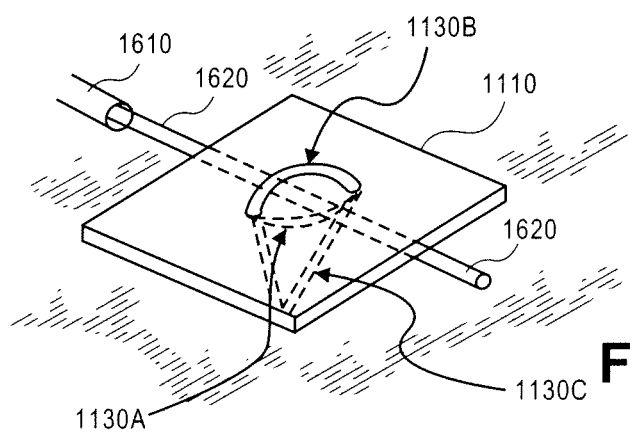
FIG. 18 shows the apparatus of FIG. 15 in another embodiment wherein a heart wire is disposed between a loop under the pledget and epicardium.

One advantage of the apparatus described in FIGS. 11-15 and the configurations presented is that a heart wire may be connected to an anchor through a loop above or below a pledget. FIG. 16 shows heart wire 1610 having electrically conductive portion 1620 disposed between pledget 1110 and loop 1130B on surface 1115 of pledget 1110. FIG. 17 shows heart wire 1610 having conductive portion 1620 disposed through loop 1130A and thus between surface 1112 of pledget 1110 and loop 1130A. FIG. 18 shows heart wire 1610 having conductive portion 1620 disposed between loop 1130A and epicardium and in electrically conductive contact with loop 1130A. Any configuration is suitable for electrically connecting heart wire 1610 to anchor 1120, though the configuration shown in FIG. 18 may be the simplest.

Figure 19:
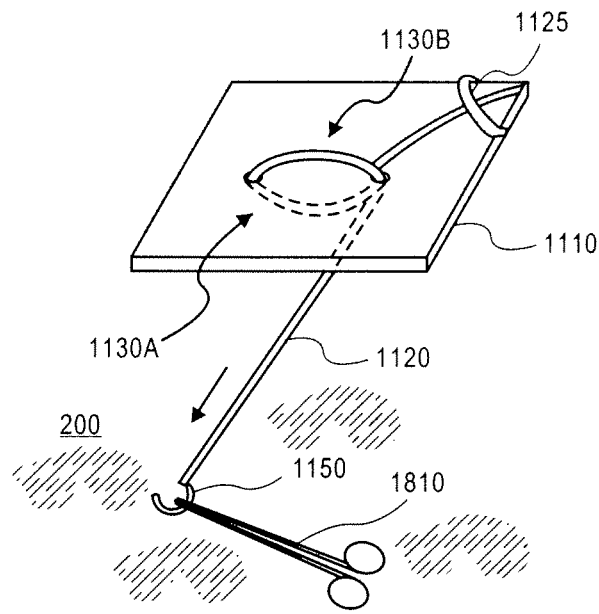
FIG. 19 shows a top side perspective view of an embodiment of an apparatus including an anchor connected to a pledget over myocardial tissue, the anchor looped twice through the pledget.
Figure 20:
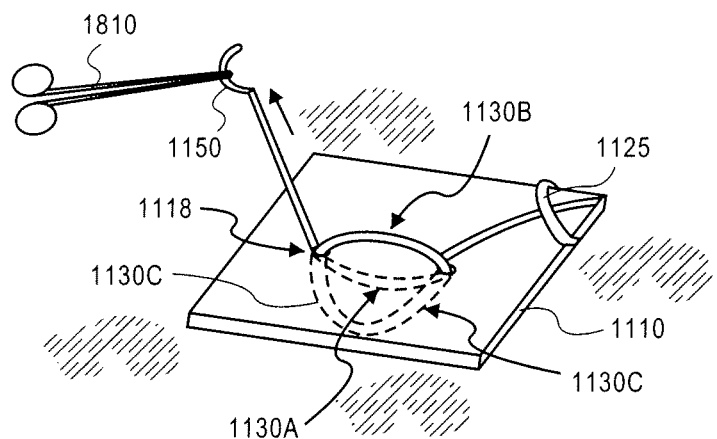
FIG. 20 shows the apparatus of FIG. 19 following the looping of the anchor through myocardial tissue and pulling the anchor through the pledget, after placing the heart wire between epicardium and a loop beneath the pledget.
Figure 21:
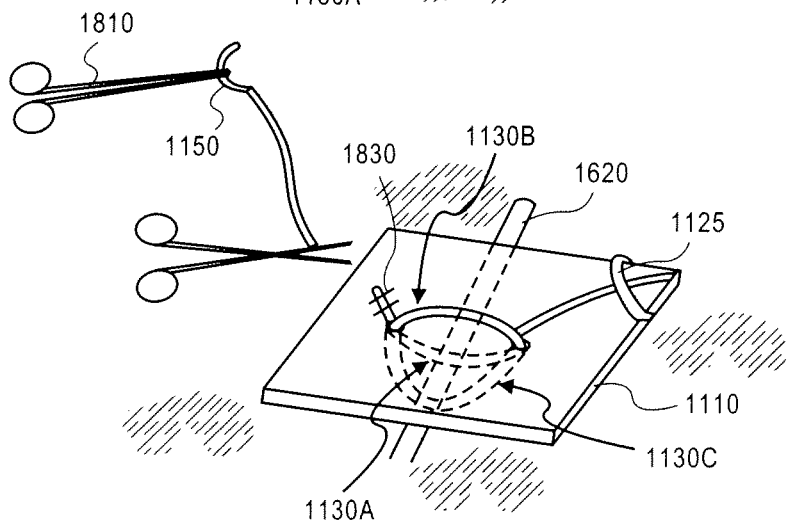
FIG. 21 shows the apparatus of FIG. 19 following the placement of a heart wire between a loop of the anchor beneath the pledget and epicardium then the securing of the apparatus to myocardial tissue.

In the embodiment described with reference to FIGS. 11-15, a surgeon loops anchor 1120 through pledget 1110 and into myocardial tissue 200. In another embodiment, an apparatus may be supplied to a physician with one or more loops already completed for the surgeon. Using apparatus 1100 as an example, FIGS. 19-21 show an embodiment where loop 1130A and loop 1130B are pre-completed. A surgeon may be provided with such an apparatus and the surgeon holds structure 1150 with needle holders 1810 and loops anchor 1120 through myocardial tissue 200 and through opening 1118 in pledget 1110. Conductive portion 1620 may then be placed (1) between epicardium and loop 1130A (FIG. 18); (2) between loop 1130A and pledget 1110 (FIG. 21); or (3) between loop 1130B and pledget 1110. Anchor 1120 is then pulled away from the tissue to tighten loop 1130A or loop 1130B against conductive portion 1620 of a heart wire to provide physical and electrical contact between anchor 1120 and conductive portion 1620. Once an electrical connection is made, anchor 1120 is fixed with clip(s) 1830 over a surface of pledget 1110 and the excess anchor, including structure 1150 may be cut with scissors 1820 and removed.

Figure 22:
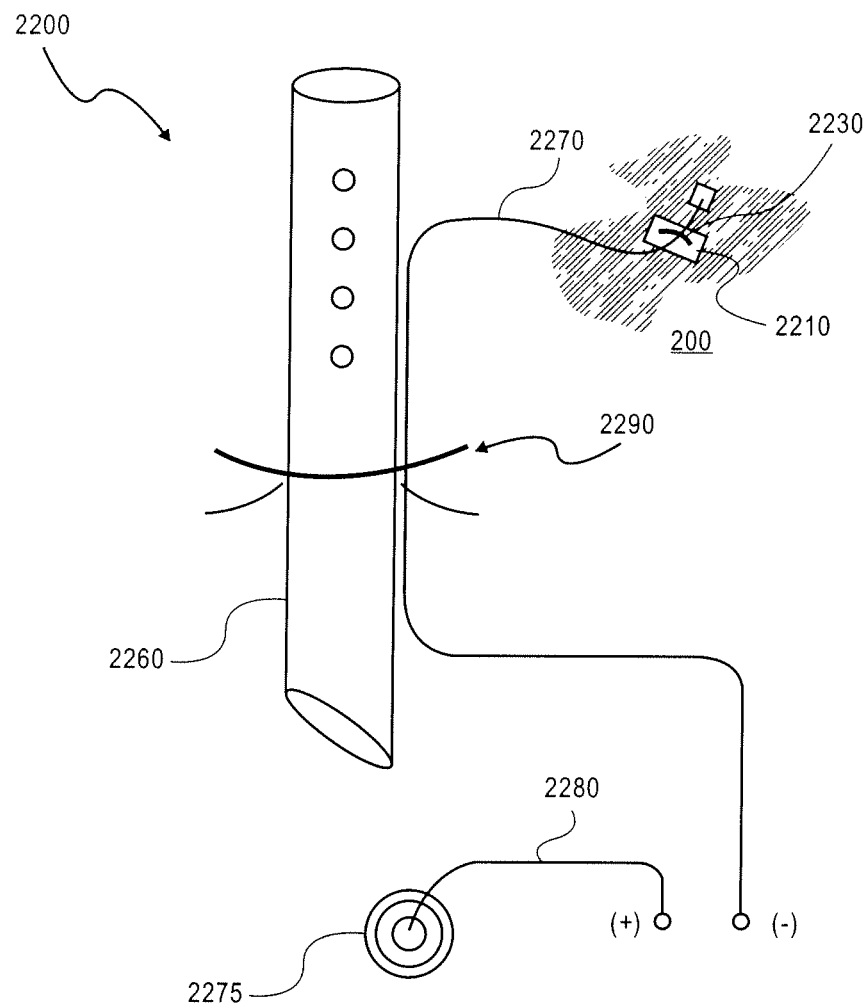
FIG. 22 shows an embodiment of a heart wire connected to a chest tube and electrically connected to myocardial tissue similar to the connection described with reference to FIG. 5 and a second heart wire connected to an electrode placed on the skin of a patient.

In many of the above embodiments related to placing heart wires, a heart wire that may serve as a negative pole is electrically connected to myocardial tissue and a second heart wire that may serve as a positive pole is connected either to heart tissue (as in FIG. 2) or to other tissue to serve as a ground. FIG. 22 shows an embodiment where a heart wire as a positive pole is connected to an electrode attached to the skin of a patient. FIG. 22 shows pledget 2210 on a surface of myocardium 200 and having conductive anchor 2230 disposed through a surface thereof and into myocardial tissue. System 2200 also includes heart wire 2270 and heart wire 2280. In this embodiment, only heart wire 2270 is connected to chest tube 2260. Chest tube 2260 is intended to be partially inserted into a patient's chest (e.g., a proximal portion of chest tube 2260 extends into the chest). Heart wire 2270 that is a negative pole is secured to chest tube 2260 and a distal end of heart wire 2270 may be pulled away from chest tube 2260 and moved to a selected position on myocardium 200. Heart wire 2270 may be attached between anchor 2230 and pledget 2210 to make physical electrical contact with anchor 2230 similar to the embodiment described with reference to FIG. 5.

In system 2200, of the two heart wires, only heart wire 2270 (a negative pole) is intended to be positioned within a chest (i.e., beyond skin level 2290) and electrically connected to myocardium 200. System 2200 also includes electrode 2275 that may be of the type used to connect precordial leads of an electrocardiogram system possibly modified to accept an end of heart wire 2280. Electrode 2275 may be placed on the skin of a patient and a conductive end of heart wire 2280 may be thereto. In this manner, heart wire 2280 is non-invasively connected to the patient (through electrode 2275).

Figure 23:
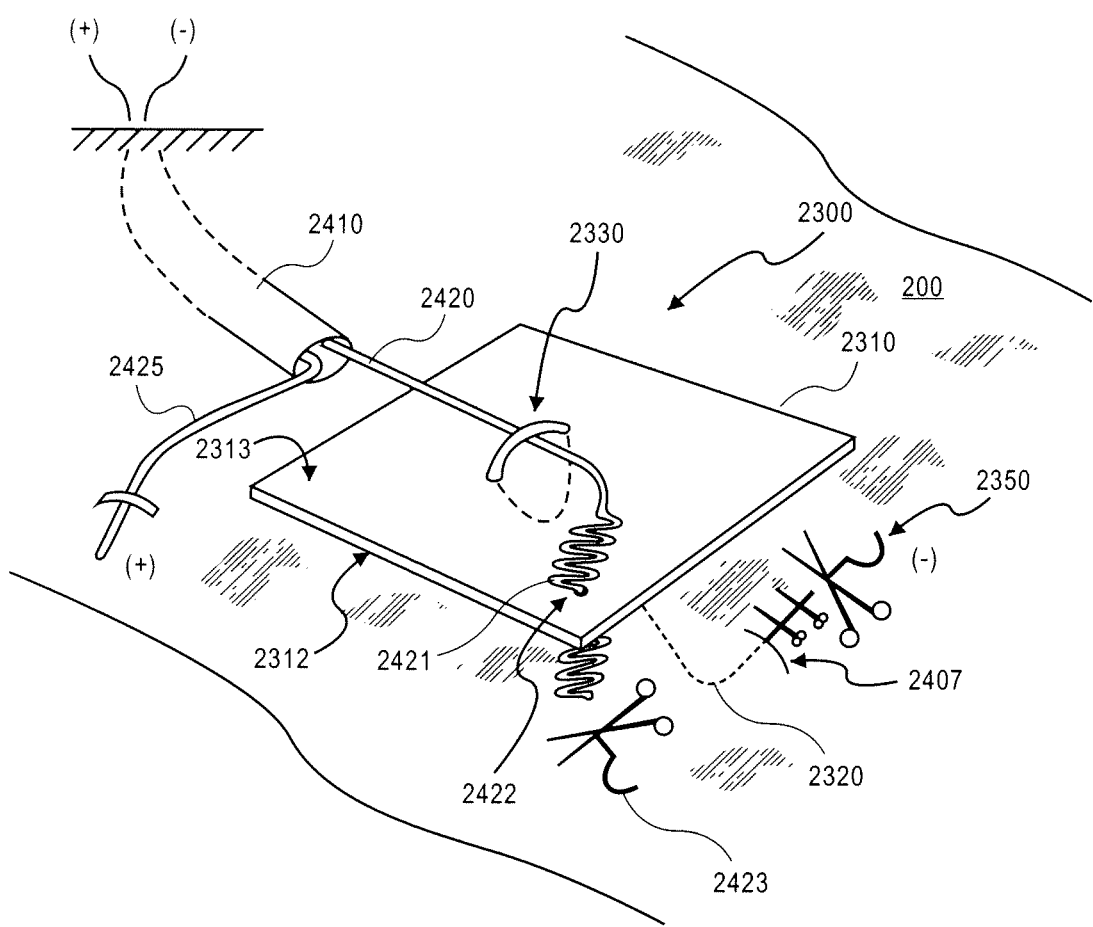
FIG. 23 shows a perspective view of an apparatus including a pledget having an anchor disposed therethrough and into myocardial tissue and a heart wire as a negative pole under a loop of the anchor and an irregular structure on an end of the heart wire partially inserted through the pledget.

In any of the above embodiments, commercially available heart wires may be electrically connected to the pledget/anchor configurations described for temporary fixation of the heart wire(s) and to minimize trauma when removing the heart wire(s). FIG. 23 shows an embodiment of an apparatus, similar to the embodiment described with reference to FIG. 1, connected to myocardial tissue. Apparatus 2300 includes pledget 2310 and anchor 2320 of an electrically conductive material disposed through pledget 2310. Anchor 2320 is disposed through pledget 2310 such that anchor 2320 forms loop 2330 over surface 2313 (a superior surface as viewed) of pledget 2310. At an opposite end, anchor 2320 includes structure 2350 such as a needle that is capable of puncturing myocardial tissue. FIG. 23 shows end 2350 inserted into and removed from myocardial tissue 200 (at point 2407) to catch a portion of myocardial tissue 200 (a portion of healthy myocardial tissue) and leave an end of anchor, including structure 2350, exposed. Structure 2350 is then removed with, for example, scissors and a remaining exposed portion is clipped with, for example, silver clips to secure anchor 2320 to myocardial tissue 200.

Following insertion of anchor 2320 into myocardial tissue 200, heart wire 2410 may be positioned on or adjacent a surface of pledget 2210. In this embodiment, heart wire includes electrically conductive portion 2420 and conductive portion 2425. Conductive portion 2420 includes at one end an irregular structure 2421 such as a zigzag of a non-conductive material (e.g., a prolene material) and end 2423 of, for example, a needle (e.g., a curved needle). Conductive portion 2420 is positioned under loop 2330 of anchor 2320 under surface 2313 of pledget 2310 and loop 2330. In this manner, electrically conductive portion 2420 is in physical contact with loop 2330 of anchor 2320.

In one embodiment, irregular structure 2421 and end 2423 of conductive portion 2420 are inserted between and beyond loop 2330 of anchor 2320 so that an electrically conductive portion of conductive portion 2420 is placed under loop 2330 of anchor 2320. Once inserted in this manner, end 2423 may be removed by, for example, scissors leaving irregular structure 2421 as an end of conductive portion 2420 with no portion of the heart wire inserted into myocardial tissue. Alternatively, as an optional configuration, once end 2423 and irregular structure 2421 are inserted between and beyond loop 2330 of anchor 2320, end 2423 and a portion of irregular structure 2421 may be pulled through pledget 2410 (at point 2422) to offer additional securing of the heart wire to apparatus 2300. In this optional alternative embodiment, end 2423 and a portion of irregular structure 2421 are pulled through pledget 2410 without being inserted into myocardial tissue 200. Once inserted in this manner, end 2423 may be removed by, for example, scissors leaving irregular structure 2421 as an end of conductive portion 2420 with no portion of the heart wire inserted into myocardial tissue 200. Of course, it is possible to insert an end of conductive portion 2420 into myocardial tissue 200, though this can lead to bleeding when the heart wire is removed. Further, if a secondary pledget is used, for example, in connection with securing an end of anchor as described with reference to FIGS. 4-5, once end 2423 and irregular structure 2421 are inserted between and beyond loop 2330 of anchor 2320, end 2423 and irregular structure 2421 may be pulled through the secondary pledget (instead of or in addition to being pulled through pledget 2310) without being inserted into myocardial tissue 200. End 2423 of a needle may then be cut.

In the embodiment illustrated in FIG. 23, conductive portion 2420 of heart wire 2410 serves as a negative pole. In this embodiment, heart wire 2410 also includes conductive portion 2425 that may be sutured on the heart or elsewhere as a positive pole.

As noted above, a commercially available heart wire may be utilized in the pledget/anchor configurations described above. FIG. 23 shows such a heart wire in a configuration similar to FIGS. 1-2. Generally, it is appreciated that a commercially available heart wire such as heart wire 2310 with an irregular structure and needle may be utilized in the pledget/anchor configurations of FIG. 3 (heart wire over anchor); FIGS. 4-5 (secondary pledget); FIGS. 6-7 (multiple end anchor); FIGS. 9 and 22 (heart wire and chest tube); FIG. 10 (AV pacing); and FIGS. 11-21 (multiple loop anchor).

In any of the various embodiments described above with reference to FIGS. 1-23, a kit may be provided to a surgeon or hospital including one or more pledgets optionally including an anchor or a kit separately including one or more anchors for one or more respective pledgets and one or more heart wires. The heart wires may be connected to one another or may be connected to a chest tube that is also provided in the kit. With the embodiment described with reference to FIG. 22, a kit may also include one or more electrodes to be placed on the skin.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. An apparatus comprising:
a pledget formed from a stitchable cloth-like material, the pledget having a length, a width, and a thickness, a first surface of the pledget configured to reside against a tissue surface of myocardium heart tissue, and a second surface of the pledget opposite to the first surface and separated from the first surface by the thickness of the pledget;
an anchor comprising electrically conductive material;
a first leg of the anchor disposed completely through the thickness of the pledget at a first location and configured to penetrate the myocardium heart tissue;
a second leg of the anchor disposed completely through the thickness of the pledget at a second location spaced apart from the first location and configured to the myocardium heart tissue, wherein ends of the first leg and the second leg join beyond the first surface and define a single end;
a loop portion of the anchor over the second surface of the pledget formed between the first location and the second location;
a heart wire having an exposed, conductive end portion residing over the second surface of the pledget and in electrical contact with said anchor through said loop through a portion of the conductive end portion above the second surface of the pledget;
wherein said heart wire is in electrical communication through said anchor into said myocardium heart tissue to conduct electrical signals into said myocardium.

2. The apparatus of claim 1, wherein the single end comprises a structure capable of puncturing myocardial heart tissue.

3. The apparatus of claim 1, wherein the heart wire is configured to not penetrate the myocardium heart tissue.

4. The apparatus of claim 1, wherein the heart wire does not penetrate the pledget.

5. The apparatus of claim 1, wherein the heart wire resides under the loop of the anchor.

6. The apparatus of claim 1, wherein the heart wire resides over the loop of the anchor and is held against the loop by sutures through the pledget.

7. The apparatus of claim 1, wherein the heart wire does not penetrate the pledget or the myocardium heart tissue and is removably retained on the second surface of the pledget by residing under the loop of the anchor and is not otherwise held in place.

8. A method comprising:

arranging a first side of a pledget formed from a stitchable cloth-like material and having a length, a width, and a thickness, to contact epicardium heart tissue of a patient;

positioning a heart wire on a second side of the pledget that is opposite the first side, the heart wire free from penetrating contact with the epicardium heart tissue;

inserting an anchor to form a loop over the second side of the pledget, and in electrically conductive contact with the heart wire;

conducting pacing signals through said heart wire and said electrically conductive anchor and into the myocardium heart tissue of the patient; and before the patient is released from a hospital following the insertion of the heart wire, pulling the heart wire out of the patient.

9. The method of claim 8, further including placing the heart wire between the loop of the anchor and the second side of the pledget.

10. The method of claim 8, wherein the pledget comprises a first pledget, the anchor comprises a first anchor and the heart wire comprises a first heart wire and the method further comprises:

placing an electrically conductive portion of a second heart wire between a second pledget and a second anchor that couples the second pledget to the myocardium heart tissue of the patient; and establishing conductive contact between the second anchor and the second heart wire.

11. The method of claim 10, wherein the first pledget is coupled to a ventricle of the patient and the second pledget is coupled to an atrium of the patient.

12. The method of claim 8, wherein the heart wire comprises a first heart wire and the method further comprises coupling a second heart wire to an electrode placed on a region of skin of the patient.

* * * * *